United States Patent [19]
Suzuki et al.

[11] Patent Number: 5,690,626
[45] Date of Patent: Nov. 25, 1997

[54] SANITARY ARTICLE WITH IMPROVED FITNESS

[75] Inventors: Migaku Suzuki, Kanagawa; Hiroaki Fukui, Saitama, both of Japan

[73] Assignee: Japan Absorbent Technology Institute, Tokyo, Japan

[21] Appl. No.: 692,371

[22] Filed: Aug. 5, 1996

Related U.S. Application Data

[62] Division of Ser. No. 298,131, Aug. 30, 1994, abandoned.

[30] Foreign Application Priority Data

Sep. 30, 1993 [JP] Japan ..................... 5-265449

[51] Int. Cl.⁶ ..................................... A61F 13/15
[52] U.S. Cl. .................. 604/385.2; 604/393; 604/396
[58] Field of Search ...................... 604/385.1–396, 604/400, 402

[56] References Cited

U.S. PATENT DOCUMENTS

| | | |
|---|---|---|
| 2,596,127 | 5/1952 | Carmean . |
| 3,608,551 | 9/1971 | Seijo . |
| 4,771,483 | 9/1988 | Hooreman et al. ............ 604/392 |
| 4,842,596 | 6/1989 | Kielpikowski et al. . |
| 4,937,887 | 7/1990 | Schreiner . |
| 5,370,634 | 12/1994 | Ando et al. ............ 604/393 |

FOREIGN PATENT DOCUMENTS

| | | | |
|---|---|---|---|
| 460461A1 | 5/1991 | European Pat. Off. ........... 604/393 |
| 3-107919 | 6/1991 | Japan ........................... 604/393 |

*Primary Examiner*—Robert A. Clarke
*Attorney, Agent, or Firm*—Kane, Dalsimer, Sullivan, Kurucz, Levy, Eisele and Richard, LLP

[57] ABSTRACT

According to the present invention, there is provided a sanitary article comprising a main body having a liquid-impermeable back sheet, a liquid-permeable front sheet and an absorbent material and leg holes having at the opposed edge portions of the main body, further comprising fixation means forming a flexible ring which are fitted closely over the entire circumference of the proximal portion of each of the wearer's legs. The article to which the present invention is directed includes both the diaper and the sanitary napkin and, hence, as the main body, either of one taking the form of underpants when worn, which has a size enough to cover the wearer's entire waist portion, and of a relatively small one which covers only the wearer's crotch portion is used. The sanitary article according to the present invention follows the wearer's movement when it is worn, and the main body does not offset from a predetermined position, but an intended absorbing effect can be displayed to the maximum extent and yet the accidental leakage cannot occur.

3 Claims, 11 Drawing Sheets

SANITARY ARTICLE WITH IMPROVED FITNESS

This is a divisional of application Ser. No. 08/298,131 filed on Aug. 30, 1994 now abandoned.

BACKGROUND OF THE INVENTION

The present invention relates to a sanitary article such as a sanitary napkin or diaper and, more specifically, to an improved sanitary article great in degree of freedom relative to the wearer's movement and which can follow the great change of his or her posture well enough.

In the sanitary article represented by the sanitary napkin or diaper, in addition to its high absorbing performance, this is expected that its fitting to and removal from the wearer's body is also easy.

Conventional sanitary articles are largely classified into two types; (1) a tape-fitted type in which it can be developed flatly by being separated at both sides of the waist portion and, when the article is fitted, the rear side waist portion and the front side waist portion are releasably coupled; and (2) a tapeless type comprising underpants in which a waist opening portion and e pair of leg holes are formed. Either type has an arrangement in which a back sheet comprising a liquid-impermeable material and a top sheet comprising a liquid-permeable material disposed internally are overlapped with an absorbent material accommodated at part therebetween and in which an elastic waist portion and leg hole portions are formed on and through the resulting main body.

Among these two types of articles, in the tape type absorbent article, it is often impossible to fit it correctly due to the wearer's low skill, and it is likely that its absorbent performance cannot be displayed fully. In addition, even if the wearer notices that they failed to correctly wear the article, it is difficult to correct the fitting due to its construction. Further, even if it is correctly fitted, it can cause a displacement due to the difference of the wearer's physical constitution or amount of movement, leading to the leakage of excretions. In order to eliminate such drawbacks, pants-type diapers have been widely spread.

On the other hand, in the sanitary napkin, ones in which, as an auxiliary fixing means, a tape is further provided to a wing which serves as means for fixing to the underwear.

However, with the foregoing diaper or sanitary napkin, a number of problems are left to be solved as regards readiness to fit and remove it and its positional stability when fitted, which are in the trade-off relationship to each other to meet.

An object of the present invention is to solve the foregoing problems inherent to the conventional sanitary articles.

SUMMARY OF THE INVENTION

According to the present invention, there is provided a sanitary article comprising a main body having a liquid-impermeable back sheet, a liquid-permeable front sheet and an absorbent material, and leg holes provided at both opposed edge portions of the main body, comprising, fixation means attached to at least part of the peripheral edge of each of said leg holes, said fixation means forming an elastic ring which fitted closely over the entire circumference of the proximal portion of each of the wearer's leg.

The present invention is directed to both diapers and sanitary napkins. Therefore, either one of the type of a size enough to cover the wearer's entire waist portion which takes the form of underpants when fitted and of a relatively small one covering only crotch portion or the wearer is used as a main body. In either main body, since the sanitary article according to the present invention is provided with fixation means which, as worn, surround the proximal portion of the wearer's leg fitting thereto, it follows his or her movement. As a result, the main body does not displace from a predetermined position, but displays an intended absorbing effect to the maximum extent without, however, causing accidental leakage of excretions.

Now, for a sanitary napkin, since it is relatively small, it is sufficient to fix to the crotch portion provisionally and then to wear shorts. However, in case of a diaper, which is large as compared with the napkin, its fitting to the leg portion alone is not sufficient to prevent its displacement and, at the same time, to fit it to the human body comfortably. As a result, it is desired to fix it at two portions; the waist portion and the crotch portion. Roles of these two fixation means are: (1) At the waist portion, it functions to fix the entire diaper to the wearer's body; and (2) At the crotch portion, it functions to follow his or her movement and yet to prevent its slip-off.

Provision of the foregoing two fixing points assures the following effect.

(a) When fitted, the article can also be worn standing as with the underpants.

(b) While fitted, the article follows the wearer's movement, the wearer can move easily, and yet, the article always maintains the sealed condition, so that it is unlikely to displace. Furthermore, the leakage of excretions can be prevented up to the limit of the absorbing capability, which greatly improves the protective performance while, at the same time, the efficiency of the absorbent material is increased.

(c) The article is fitted to the wear's body at waist portion and the proximal portions of the legs, so that it is possible to lower the restriction force, and hence the contacting force of the waist and leg gathers can be small, resulting in preventing forming of waist line or mark on the wearer's body.

(d) Comparing to the conventional pants-type diapers, the connecting force at the side seal portions can be lowered, so that it can easily be peeled off at the connecting portions upon taking off of the article.

(e) Due to the dispersion of force, it is not necessary to press in with a strong force, and the amount of the tape or elastic member to be used can be greatly reduced, and yet its absorbing effect is increased. As a result, it is easy to construct s structure suitable for the so-called ultrathin type, reducing the manufacturing and selling cost greatly.

This structure, since both fixed sites are independent of each other and the elastic efficiency works without causing any interference of forces relative to each other, allows various structure designs, so that it is unlikely to become stuffy because it poses less constraint to the wearer, especially the infants, and assures ease to move and relaxed feelings. Furthermore, it is easy for mothers to make her baby wear it or to take it off from the wearer.

DETAILED DESCRIPTION OF THE PREFERRED EMBODIMENTS

Figure 1:
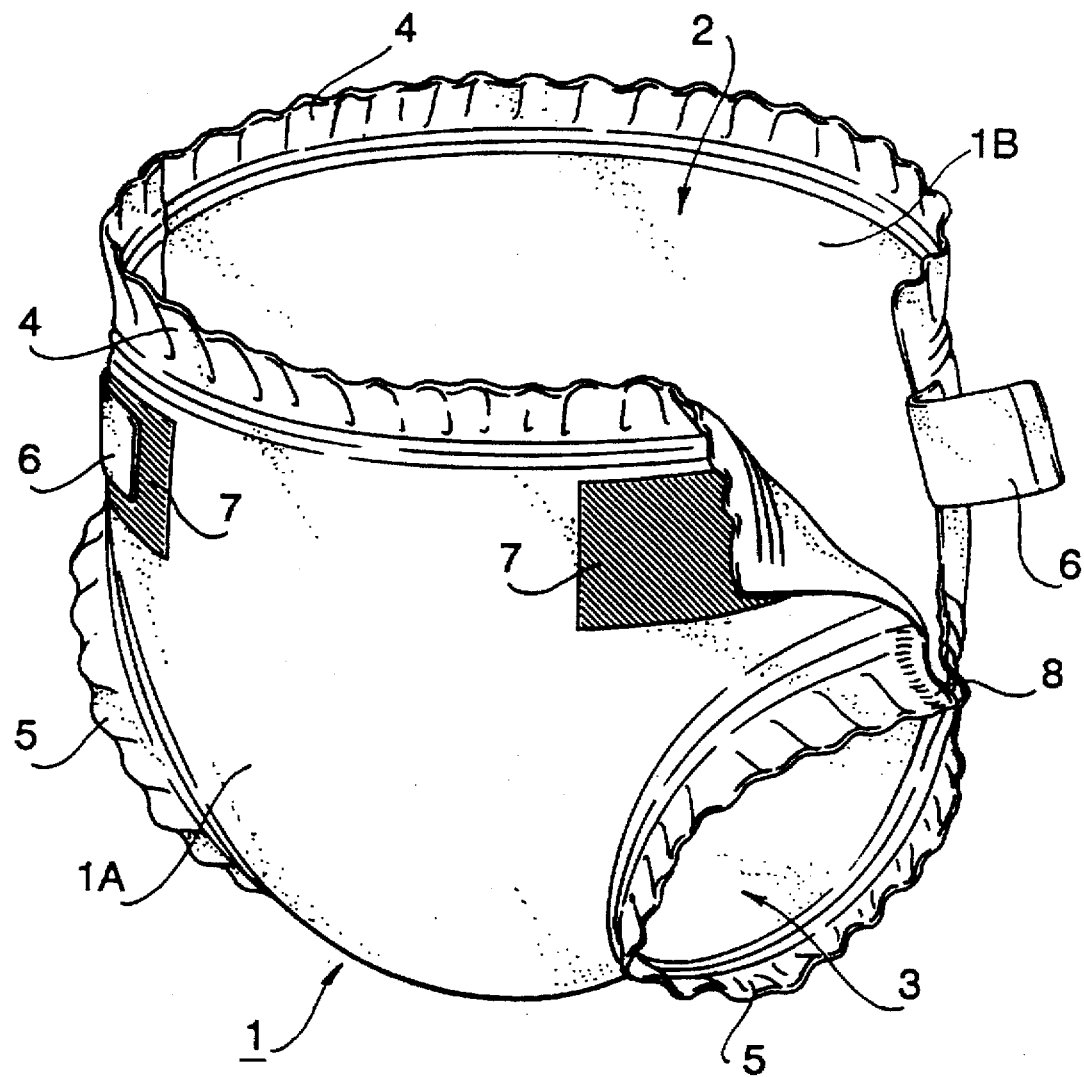
FIG. 1 is perspective view illustrating a sanitary article taking the form of a diaper according to a first embodiment of the present invention.

FIG. 1 illustrates e perspective view of a sanitary article in the form of a diaper according to the present invention, in which the main body generally indicated by a reference numeral 1 comprises an arrangement in which a back sheet comprising a liquid-impermeable material and a top sheet comprising a liquid-permeable material, which is disposed internally, are overlapped so that an absorbent material is accommodated therebetween and in which a waist hole and two leg holes are formed.

The main body 1 comprises a front portion 1A and a rear portion 1B with the central portion of a substantially rectangular sheet member running in the lengthwise direction taken as the boundary. With the sanitary article worn, the front portion 1A covers the wearer's belly portion, the rear portion 1B covers his or her hip portion, their boundary portion covers the lower portion of the crotch, the arc formed by both end portions of the short side of the main body forms a waist hole 2 and a pair of leg holes 3 are formed between two long sides of the main body.

Furthermore, the main body includes fixation means 5 comprising elastic rings are provided, which extend along the peripheral edge of each leg hole. In this embodiment, the fixation means 5 is arranged by joining a band-shaped elastic sheet of appropriate width, which presents a resiliency at least in the lengthwise direction, along the peripheral edge of the leg hole of the main body 1, to couple its both ends at a coupling portion 8. A preferred means to couple at the coupling portion 8 is a hot melt-type adhesive agent.

Preferably, elastic band-shaped waist gathers 4 having a proper width may be attached to the main body along the peripheral of the waist hole 2.

Numeral 6 denotes coupling means or a tape attached at the lateral edge of the rear portion 1B between the waist gathers 4 and the leg gathers 5. Each tape 6 constitutes a fastener together with a receiver member 7 attached on the outer surface of the front portion 1A. Each of the tapes 6 are coupled to the receiver member 7, respectively, before the article is worn, so that the main body 1 is made to take the form of pants-type diaper, with its front portion 1A and rear portion B being each coupled at part of each lateral edge. The tapes used in this embodiment constitutes a fastener tape having a multiplicity of hooks and loops which is generally called as "a magic tape" and commercially soled by Kuraray Corporation, Japan, under the trademark "VELCRO".

In such sanitary article, before worn, the tapes 6 are coupled to the respective receiver members 7. Therefore, it takes the form of underpants as a whole, and can be pulled on in the sequence similar to that with the ordinary underwear. When worn, the fixation means 5 allows the leg to be readily inserted therethrough by its own elasticity and, when the article has been fitted to the body, it is closely fitted to the circumference of the proximal portion of the leg to be retained there stably. Retaining of the fixation means 5 at a predetermined position means that the main body 1 to which it is attached is also stably retained in position to the wearer, so that a stable fitting condition of the article, which is one of the important advantages of the present invention, can be realized.

Another important advantage of the present invention is that since the fixation means 5 presents a certain degree of displacement or a degree of freedom of deformation relative to the main body 1, even if any displacement occurs between the wearer's trunk and leg due to the wearer's movement, the main body follows the trunk while it cannot virtually happen that the fixation means retained to the proximal portion of the leg is pulled toward the main boy, so that there is no danger that the stable fitting condition is disturbed.

Figure 2:
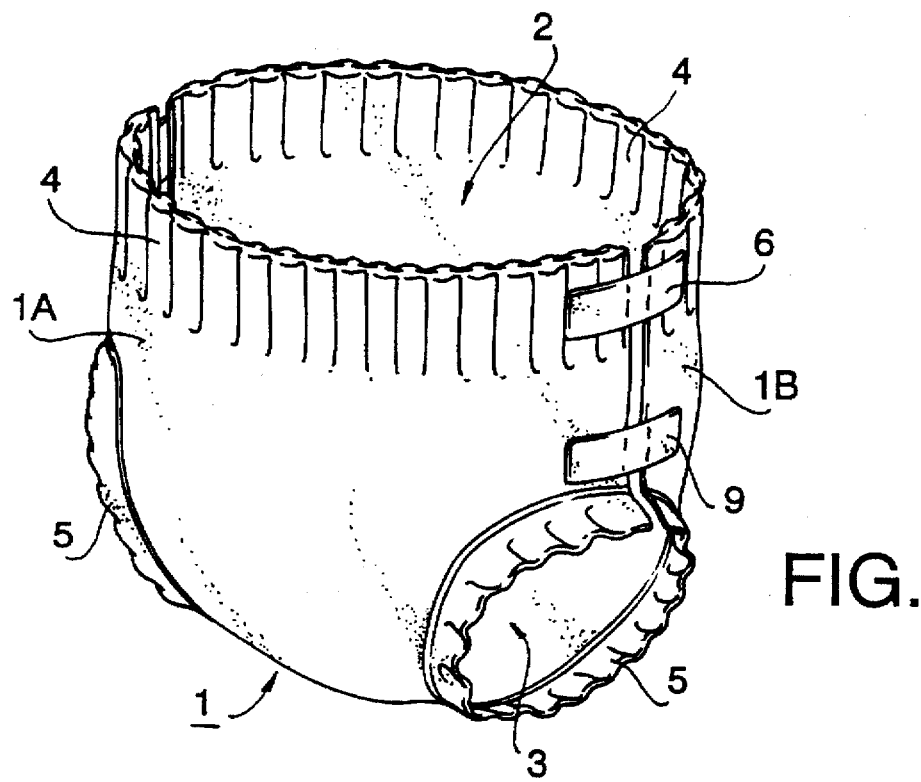
FIG. 2 is a perspective view of the sanitary article in the form of a diaper according to an alternate embodiment of the present invention.

FIG. 2 illustrates an embodiment in which, as means constitute the ring-shaped fixation means 5 by coupling both ends of the band-shaped elastic sheet member, tapes 9 are used in place of the adhesive agent applied in the embodiment of FIG. 1.

Figure 3:
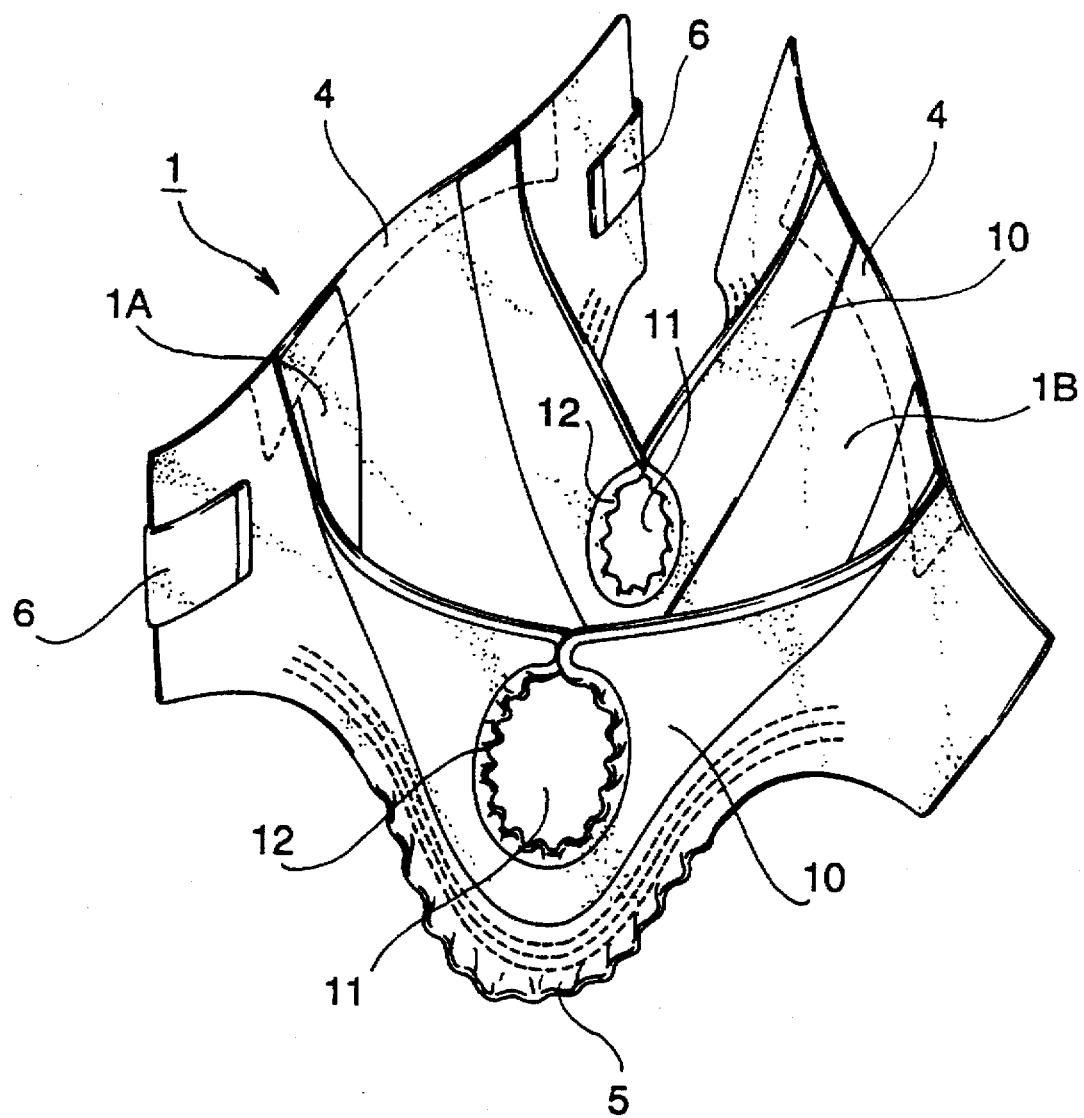
FIG. 3 is a perspective view of the sanitary article in the form of a diaper according to a third embodiment of the present invention.

FIG. 3 illustrates a sanitary article according to a third embodiment of the present invention in the state in which the tapes 6 are released from the receiver members (not visible in this figure) to open the lateral edges of the front portion 1A and the rear portion 1B slightly spaced apart from each other. Here, the same or similar portions as in FIG. 1 are indicated by the same reference numerals.

As seen from FIG. 3, a pair of side members 10, each comprising an elastic sheet member, is provided internally of the main body 1 so as to extend along both lateral edges thereof. Each side member 10 is widest at the portion lying at the center of the thigh portion of the main body, and is narrowed at the side of the waist hole and, when the article is fitted, functions as the internal standing gathers. An opening 11 is formed at the widest portion of the side member, that at the portion corresponding to the leg portion of the main body so as to pass the wearer's leg through.

A band-shaped elastic sheet member is attached along the circumference of the opening 11 so as to form a ring 12, and the ring constitutes a fixation means together with the side member.

As the material forming the side member 10, it is preferable to use a sheet material which is pleasant to feel the human body and which has a proper elasticity, flexibility and leak-proof property. Examples of these material includes a nonwoven fabric, or a composite of the nonwoven fabric and a elastic material having a proper flexibility and elasticity. An elastic film may also be used, but it is often used together with a nonwoven fabric or the like, since it contacts to the skin directly.

As the elastic nonwoven fabric, those obtained by confounding fibers such as made of polyester, polypropylene or the like with a card web containing highly shrinkable conjugate fibers by water jet and subsequently, by subjecting it to a heat shrinkage process may be used. A preferably elastic composite material may be of a nonwoven fabric and a elastic film, or a nonwoven fabric and an elastic melt blown. As the side member, an air-breathing stock is more preferable and, as desired, it is also effective to provide a plurality of small vent above the side member at the sites excluding the danger of the liquid leaching in order to prevent getting steamy.

Figure 4:
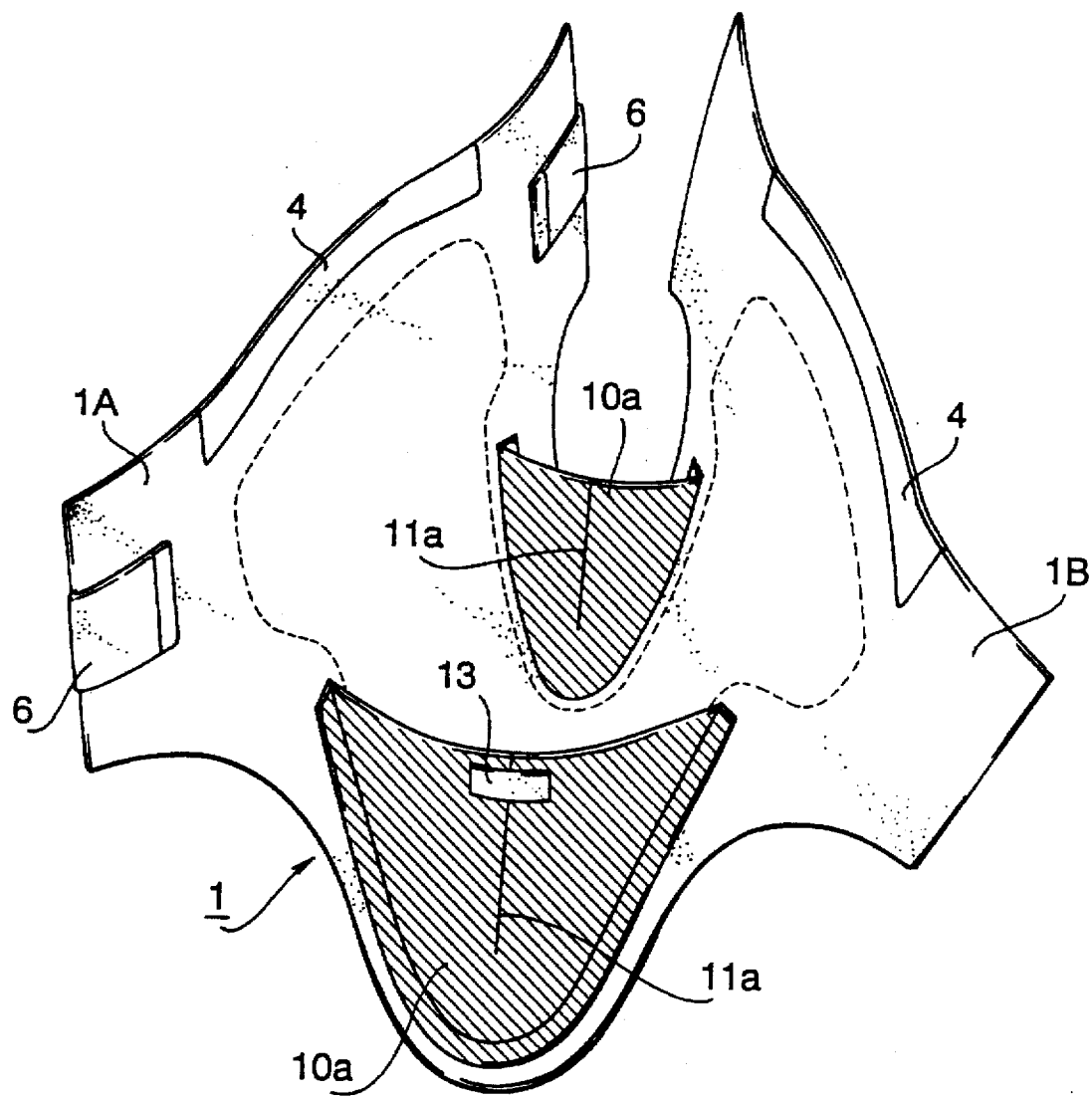
FIG. 4 is a perspective view of the sanitary article in the form of a diaper according to a fourth embodiment of the present invention.

FIG. 4 illustrates a fourth embodiment of the present invention in which a pair of side members 10a are used. Each side member comprises an elastic sheet material at its upper edge having a slit 11a of proper length, and the open end of the slit 11a is closed with a tape 13. In this embodiment, the side member per se functions as the fixation means relative to the wearer's leg passed through the slit 11a, that is, the leg hole provided through the side member 10a.

Figure 5:
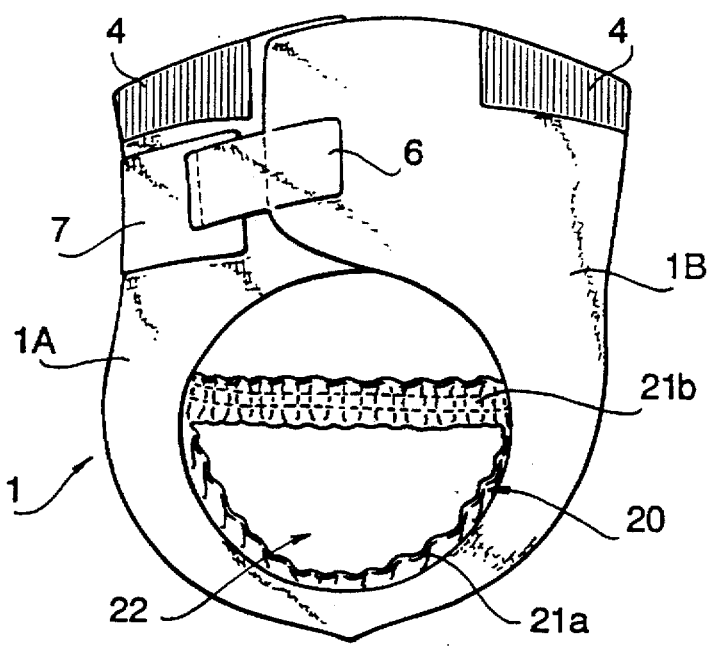
FIG. 5 is a perspective view of the sanitary article in the form of a diaper according to a fifth embodiment of the present invention.
Figure 6:
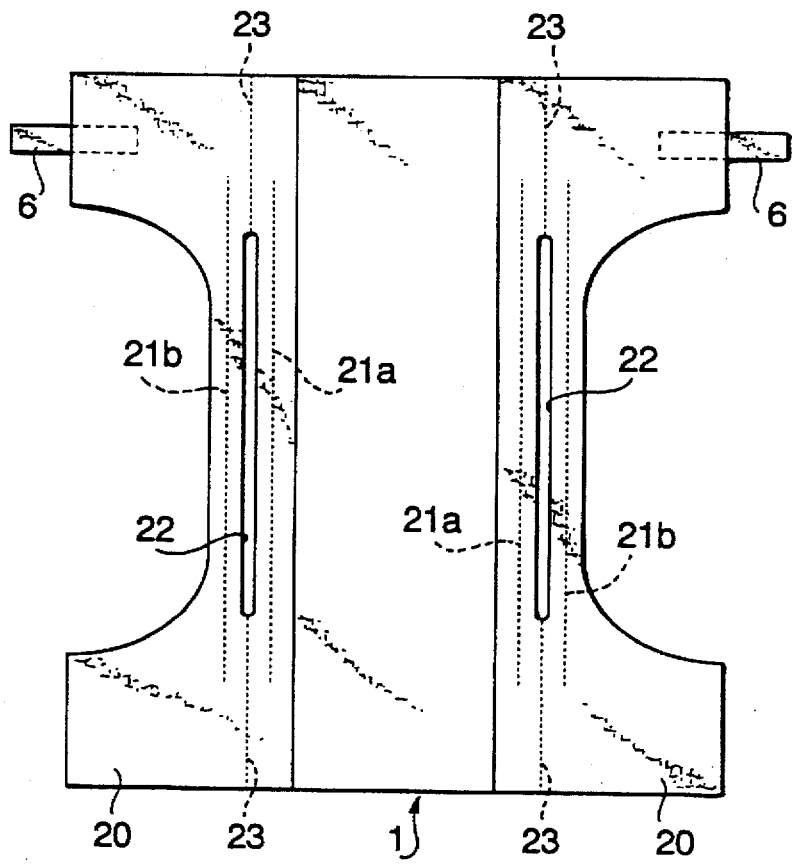
FIG. 6 is a developed plan view of the article of FIG. 5.

FIGS. 5 and 6 illustrate a sanitary article according to a fifth embodiment of the present invention. The main body 1 used in the sanitary article of this embodiment is basically the same as that of the previous embodiments, and a pair of fixation means 20 as explicitly shown in FIG. 6 is provided internally of the main body. Each fixation means 20 comprises a sheet material of such a size enough to cover about one third of the inner surface of the main boy, the inner lateral surface of the main body is exposed at the portion not covered by the fixation means, and an absorbing zone is formed there.

The outer lateral edge portion of each fixation means 20 extends along the edge portion of the main body 1 and between the outer lateral edge portion and the inner side edge portion, a slit or an opening 22 is formed extending in the lengthwise direction. Each fixation means 20 is joined to the main body 1 only at its outer side edge portion and is not joined at is inner side edge, so that the space or pocket formed therebetween is in communication with the exterior at the inner lateral edge and the slit 22.

Preferably, two sets of elastic members 21a and 21b are provided at both sides of the slit 22 so as to extend in parallel to the slit 22, although they are not necessarily needed if the sheet member per so, which constitutes the fixation means, has a sufficient elasticity. Furthermore, it may be desirable to provide perforations 23 at the fixation means 20 so that they extend from both ends of the slit 22 up to both ends of the fixation means. These perforations 23 make it easy to increase the size of the slit 22 according to the thickness of the proximal portion of the wearer's leg while serving to further make it easy to tear the fixation means 20 off when the article is released.

FIG. 6 illustrates a condition in which the elastic member 21a, 21b are stretched. If its both ends are released from the stretched condition, the elastic members 21a, 21 contract in their length due to their restoring forces and, when the article is actually worn, as shown in FIG. 5, provides annular fixation means connected to the elastic members for the proximal ends of the legs of the wearer legs, great in the freedom of movement relative to the main boy 1. In the above embodiments, since necessary fixation is done by the fixation means at the legs, the article does not slip down, even if the tape which is fixation means at the waist portion is removed. This makes a great advantage when checking of excretion is necessary.

In the foregoing embodiments, in order to couple the front portion 1A and the rear portion 1B of the main body, in order to complete the ring-shaped opening to the side member, the tape is used. As the tape, those having an ordinary arrangement or the aforementioned "VELCRO" type fasteners may be used. Put those used in FIGS. 7 to 10 are suitable for attaining the object of the present invention.

Figure 7:
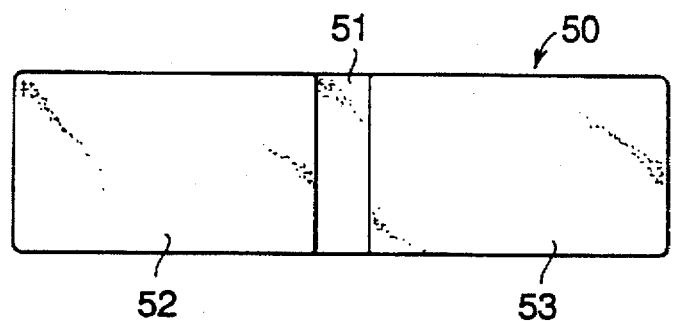
FIG. 7 is a plan view of a releasable tape which is used in the sanitary article of the present invention.
Figure 8:
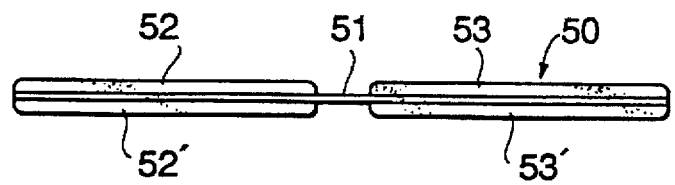
FIG. 8 is a side view of the tape of FIG. 7.

The tapes 50 shown in FIGS. 7 and 8 have an arrangement in which non-elastic sheets 52, 52' are adhered on both surfaces of one end portion of a substantially rectangular sheet-shaped elastic member 51, which is excellent in elasticity, and similar sheets 53, 53' are each adhered on the other end, and exhibits an elasticity at the portion not covered by the sheet alone. This elastic tape 50 is firmly adhered to the edge portion of the front portion 1A of the main body 1 by the sheet 52 (or 52') at one end portion and to the edge portion of the rear portion 1B by the sheet 52 (or 52') at the other end portion.

Figure 9:
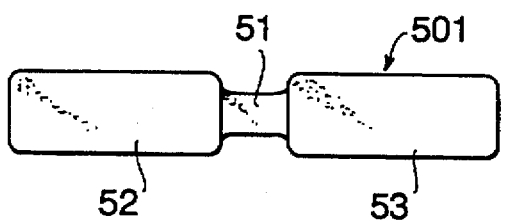
FIG. 9 is a plan view of another releasable tape which is used in the sanitary article of the present invention.
Figure 10:
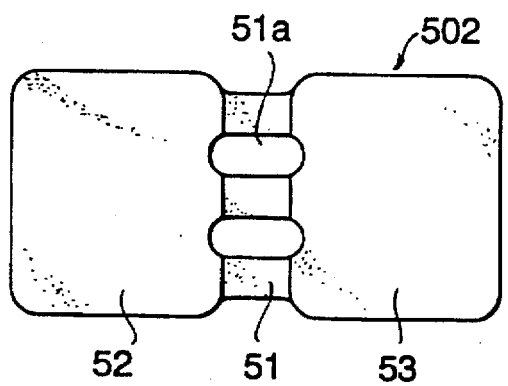
FIG. 10 is a plan view of a still another releasable tape which is used in the sanitary article of the present invention.

In the tape shown in FIG. 9, the width of the portion of the sheet-like elastic member 51 which is not covered by the non-elastic sheets 52, 52' is made small to make the elasticity of the portion great. Alternatively, the same object may also be achieved by providing one or more holes 51a at the portion of the sheet-like elastic member 51 which is not covered by the non-elastic sheets 52, 52'.

Figure 11:
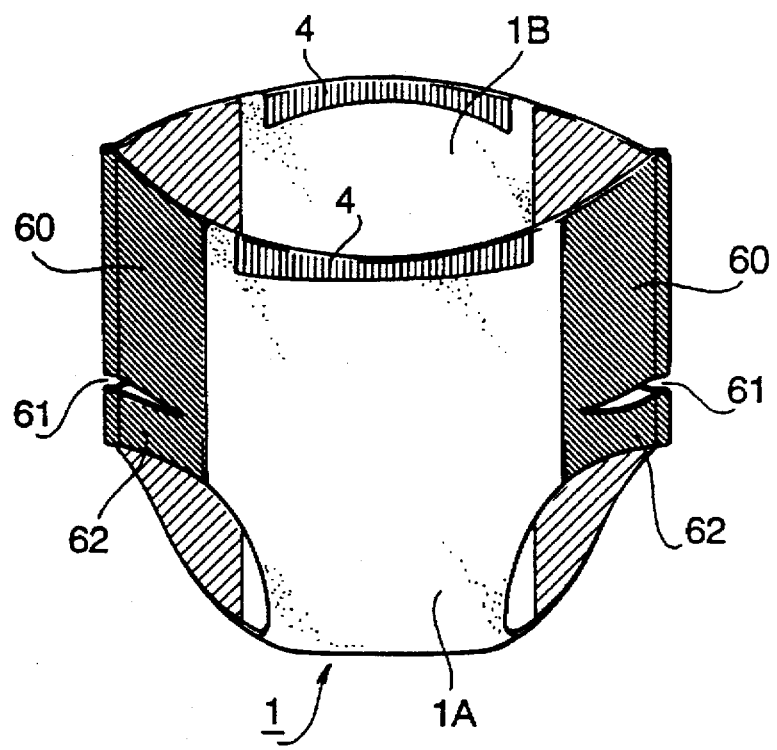
FIG. 11 is a perspective view of the sanitary article in the form of a diaper according to a sixth embodiment of the present invention.

FIG. 11 illustrates a sixth embodiment of the present invention provided with another fixation means which is great in degree of free movement or displacement relative to the main body. In this embodiment, the substantially rectangular main body 1 forms the front portion 1A and the rear portion 1B, bent into U-shape, and is coupled to both sides of the front portion 1A and the rear portion 1B by means of the side member 60 comprising an elastic sheet member, which interconnects the lateral edge portions opposed to each other. Leg holes are formed by cut out part: of the main body and the side member 60.

Further, a cut out or a slit 61 is formed at the side member 60 at the position slightly below its lower end. This slit extends up to the neighborhood of its beth lateral edge in the width direction of the side member, so that a narrow band-shaped portion 62 which is cut apart from the remaining portion is formed at the lower end portion of the side member, and serves as the fixation means.

Figure 12:
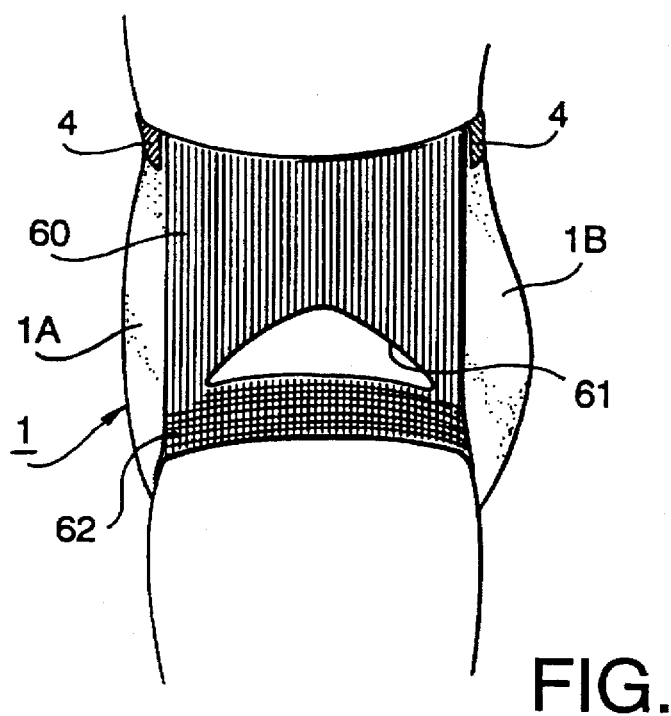
FIG. 12 is a perspective view illustrating how the sanitary article of FIG. 11 is worn.

FIG. 12 illustrates a condition in which the sanitary article of FIG. 11 is worn. As seen from this figure, when the article is worn, the side member 60 retains the front portions 1A and 1B of the main body 1 to the wearer's waist portion by cooperating with the waist gathers, and the band-shaped portion 62 forms a ring-shaped fixation means together with the crutch portion of the main body 1 to fix the article at the proximal portion of the wearer's legs.

Figure 13:
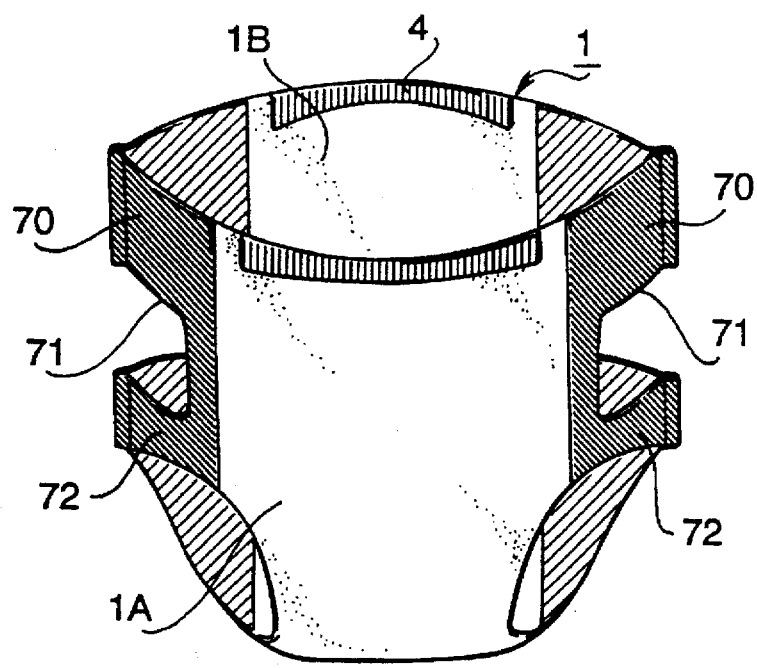
FIG. 13 is a perspective view of the sanitary article in the form or a diaper according to e seventh embodiment of the present invention.
Figure 14:
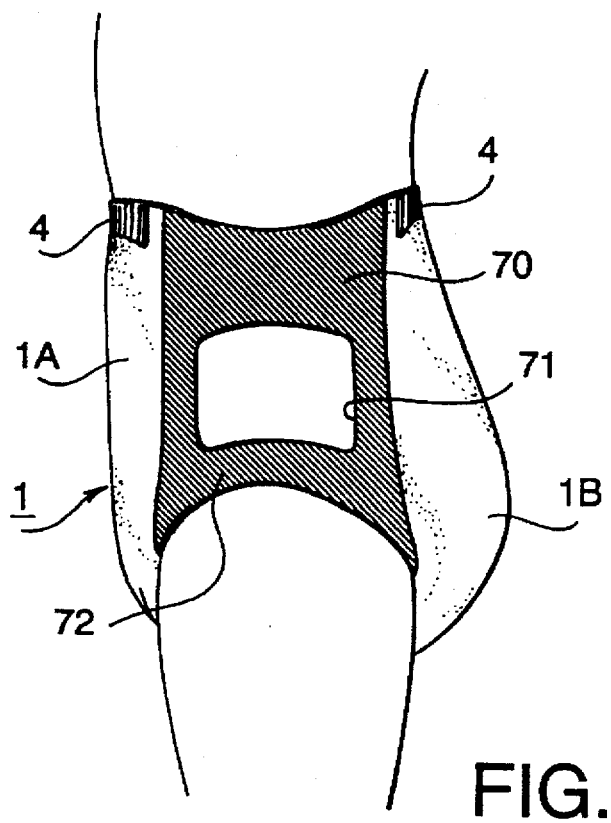
FIG. 14 is a perspective view illustrating how the sanitary article of FIG. 13 is worn.

FIG. 13 illustrates a seventh embodiment of the present invention, which shows a side member 70 formed with a larger opening 71 as compared with one shown in FIG. 11. Each band-shaped portion 72 separated by the opening 71, when the article is worn as in FIG. 14, functions as the fixation means which fixes the article at the proximal portion of the wearer's legs.

In the articles shown in FIGS. 11 and 13, since the front portion 1A and the rear portion 1B of the main boy are coupled by means of the side members, unlike those coupled by the foregoing tapes, they are difficult to take off. In order to eliminate this disadvantage, in the illustrated embodiments, the side member comprises two parts connected at the Joining lines running from its upper end to the lower end by means of the adhesive agent. The joining line has a sufficient bonding strength with which the article is not broken while being worn and used, but can be torn apart by pulling strong when removed.

Figure 15:
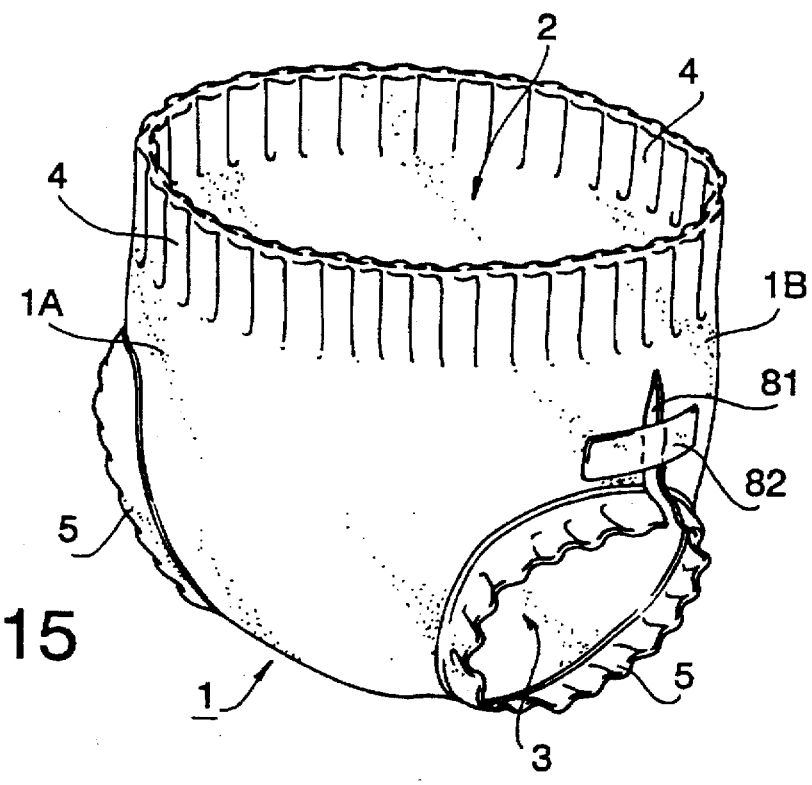
FIG. 15 is a perspective view of the sanitary article in the form of a diaper according to the seventh embodiment of the present invention.

Otherwise, as shown in FIG. 15, a slit 81 is formed across each of a ring 5 comprising an elastic band-shaped sheet member disposed along the peripheral edge of the respective leg hole 3, which is formed at the main body 1 and reaching part of the main body 1 contacting the ring. Each slit is fixed in a closed state by a tape 82 attached across the slit 81 so as not to open.

In this embodiment, the ring 5 and the tapes 82 provide closed fixation means 5. The tapes 82 act as fixation means which can be removed to make the main body in to a skirt-like shape upon wearing, and also can be fastened during wearing. Upon taking off, the tapes can be unfastened, thereby to make possible to handle the article without the shoes or socks from becoming dirty.

The present invention may be applied to the sanitary article taking the form of napkin, other than those of the diaper as mentioned above.

Figure 16:
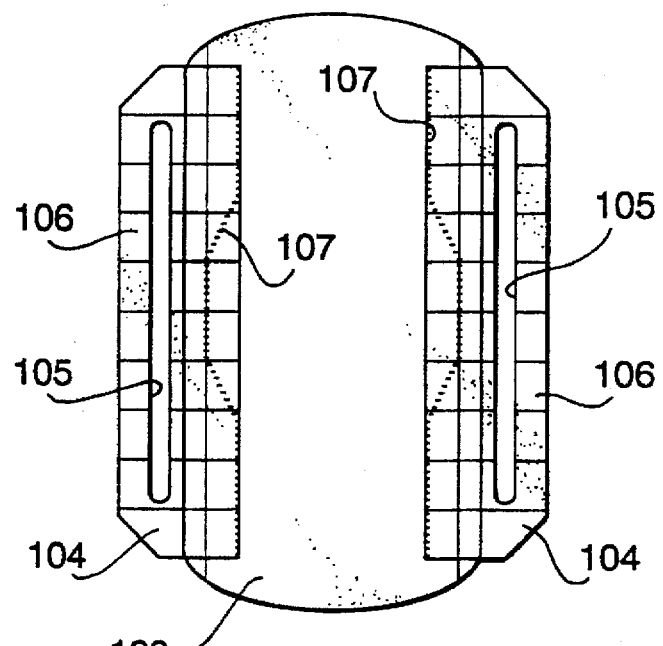
FIG. 16 is a plan view of a sanitary article in the form a sanitary napkin according to an embodiment of the present invention.
Figure 17:
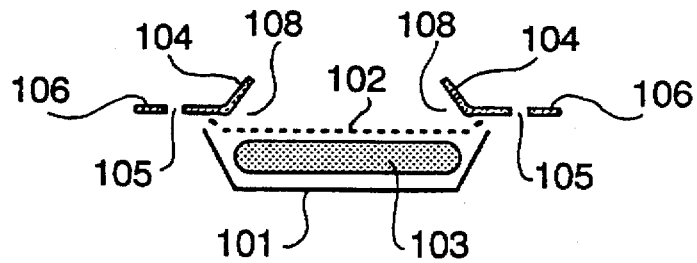
FIG. 17 is a longitudinal cross-sectional view of the article of FIG. 16.
Figure 18:
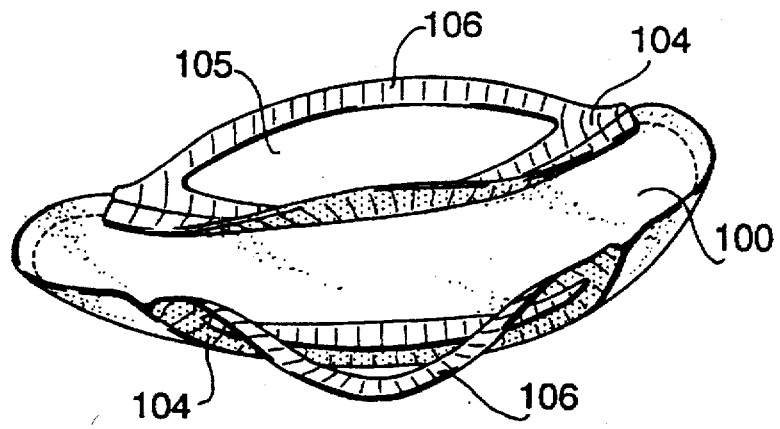
FIG. 18 is a perspective view of the article of FIG. 16.

In FIGS. 16 to 18, a main body 100 is of rectangular form in which a liquid-impermeable sheet 101 and a liquid-permeable sheet 102 are coupled together at their peripheral edge and an absorbent member 103 is disposed therebetween. At both sides of the main body, a thin and elongated band-shaped side members 106 comprising an elastic sheet member is attached.

Each side member 104 is formed with a thin and elongated opening 105 which extends in the lengthwise direction of the member to segment a thin and elongated portion 106 lying at the outside of the opening. The portion lying at the inside of the opening 105 is coupled to the main body 100 at the joining line 107. The joining line extends along its innermost edge portion but, at the central portion, extends so as to lie at the inner side. Therefore, the central portion serves as a standing cuff to form a pocket 108 between the same and the surface of the main body acting to prevent side leakage.

Figure 19:
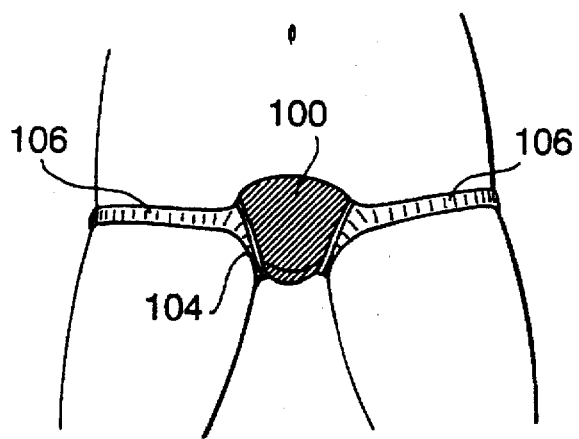
FIG. 19 is a front elevation illustrating how the article Of FIG. 16 is used.
Figure 20:
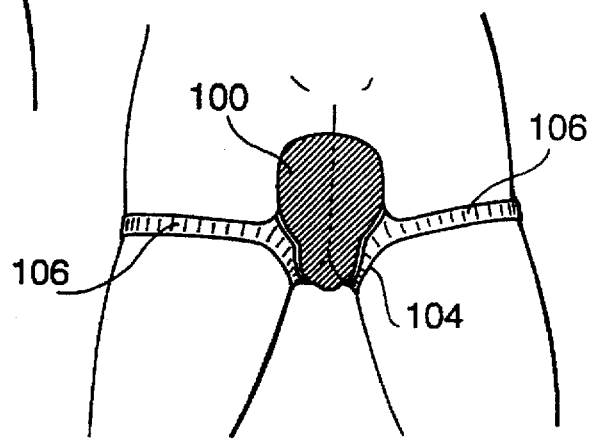
FIG. 20 is a rear elevation of the article of FIG. 16 how it is used.

Such an article is worn by inserting the wearer's legs into the respective openings 105. The state in which the article is worn to a predetermined position is shown in FIGS. 19 and 20. As seen from these figures, the side member 104 serves as ring-shaped fixation means surrounding the proximal portions of the wearer's legs to fix the main body at a predetermined position stably.

Figure 21:
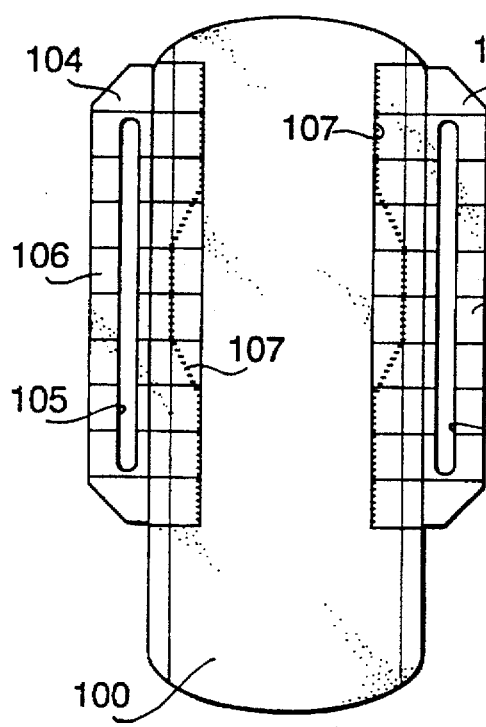
FIG. 21 is a perspective view of an alternate embodiment of the sanitary article in the form of a sanitary napkin shown in FIG. 16.

FIG. 21 illustrates a sanitary article taking the form of the same napkin as that of FIG. 16 except that the length of the used main body 100 is elongated.

Figure 22:
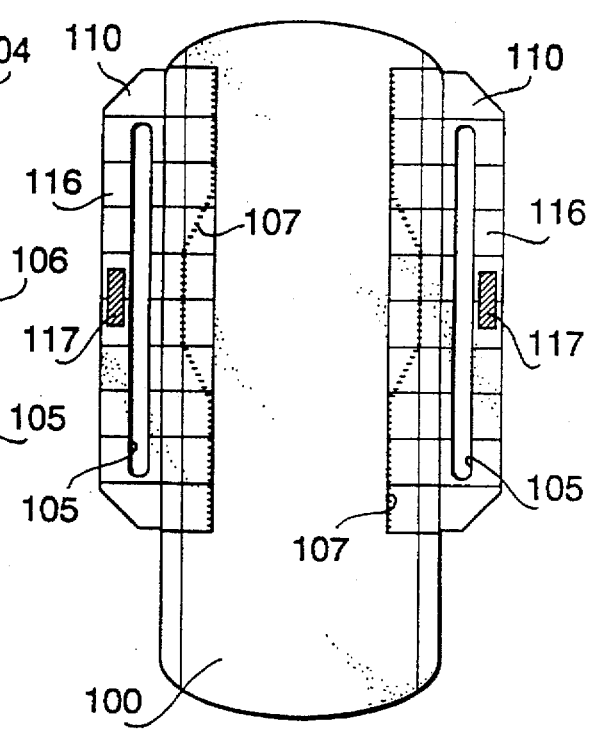
FIG. 22 is a perspective view of another embodiment of the sanitary article shown in FIG. 16.

FIG. 22 illustrates a sanitary article taking the same form of napkin as one shown in 21 which is provided with side members 110 taking another form. In each side member 110 used in this embodiment, the portion 116 lying at the outside of the slit 105 is cut apart at a proper position as viewed in its lengthwise direction, and =he opposed end portions are coupled releasably by means of a coupling tape 117.

The sanitary article shown in FIG. 22 can be fitted by inserting the legs through the slits 105, as in one shown in FIG. 21, but may be fitted by forming rings by coupling their free end portions with the coupling tapes 117 after the portions 116 are disposed so as to surrounding the proximal portions of the legs.

Figure 23:
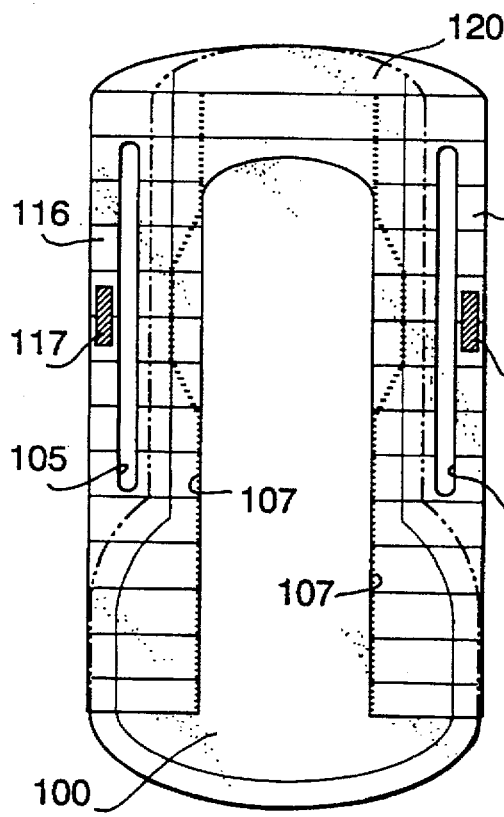
FIG. 23 is a perspective view of yet another embodiment of the sanitary article shown in FIG. 16.

FIG. 23 illustrates a sanitary article of the present invention which is further provided with the main body 110 of another form and a side member 120. In this embodiment, each of side members 120 takes a substantially U-form, and the portion 116 separated from the other portion at the slit 108 is each formed at its holes. The portion 116 may be continuous but, alternatively, may be cut apart at the central portion, and the opposed free ends may be coupled releasably by means of the tape 117, as in the embodiment of FIG. 22.

Figure 24:
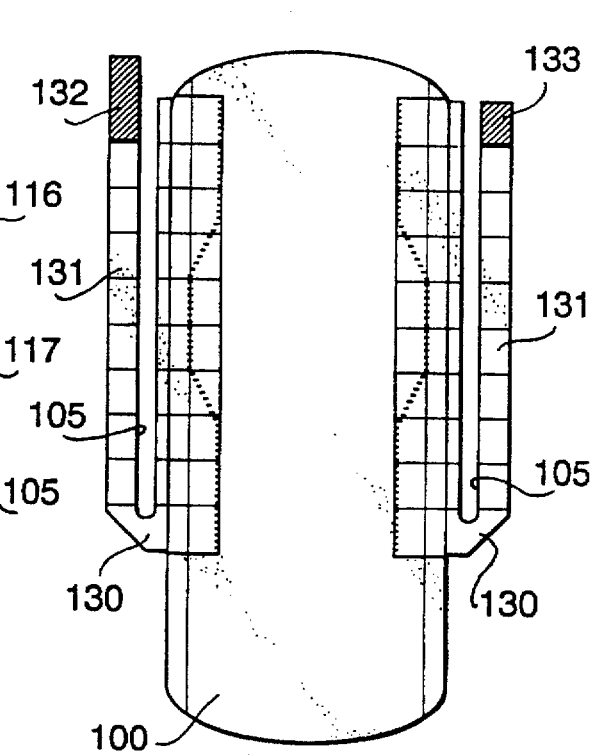
FIG. 24 is a perspective view of still another embodiment of the sanitary article shown in FIG. 16.

Alternatively, as show in FIG. 24, a side member 130 in which one end of the slit 105 is in communication with the exterior and in which the other is formed into a free band-shaped portion 131 may be used. A tape 132 is provided at the free end of each band-shaped portion 131 and, after the main body 100 is set to a predetermined position, the tape 132 is coupled to a proper position of the side member to complete a ring-shaped fixation means.

Figures 25A, 25B:
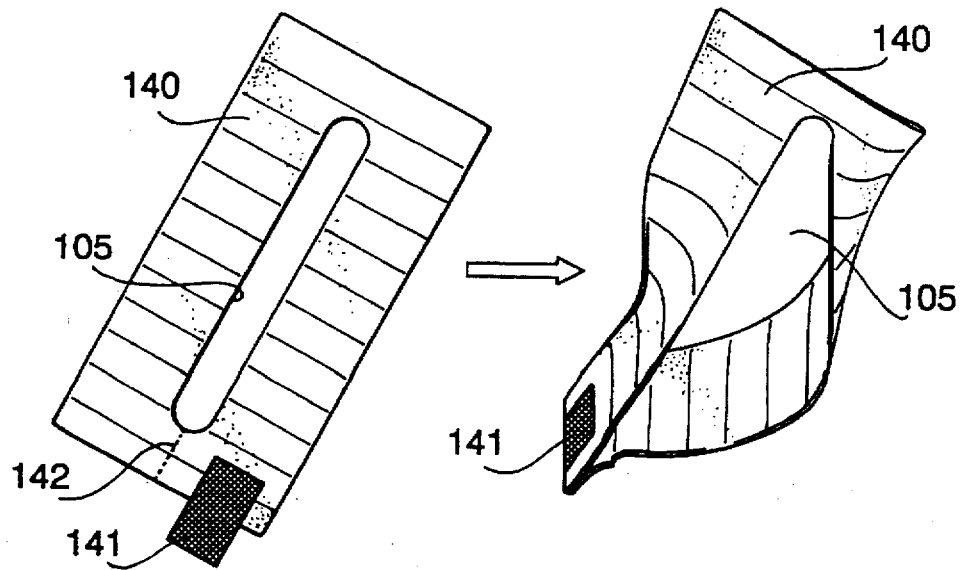
FIG. 25A is a perspective view of another side member, prior to use, which is used in the article in the form of the sanitary napkin according to the present invention.
FIG. 25(B) is a perspective view of the side member shown in FIG. 25(A) during use.

Further, FIG. 25(A) and 25(B) illustrates one of side members 140 which is attached to both sides of the main body (not shown). The side member 140 is band-shaped having a thin and elongated slit 105 extending along the centerline passing through the center as viewed in the width direction, and a tape 141 is attached at one end portion of two areas which are segmented by the centerline.

Although, as shown in FIG. 25(A), prior to use, the side member 140 is folded back along the following line 142 lying on the centerline while the article is worn, so that, as shown in FIG. 25(B), the overlapped end portions are coupled by means of the tape 141.

What is claimed is:

1. A sanitary article comprising a main body having a liquid-impermeable back sheet, a liquid-permeable front sheet and an absorbent material, and leg holes provided at both opposed edge portions of the main body, said main body divided into a front portion and a rear portion along the lines running from said waist hole up to each leg hole, and both side edge portions of said front portion and both side edge portions of said rear portion which are opposed thereto are coupled by tapes; comprising a pair of side members each extending along the peripheral edge of said leg hole at the inner side of said main body, and having an opening formed at the portion corresponding to the leg hole of the main body so as to pass the wearer's leg through, thereby to form fixation means surrounding closely over the entire circumference of the proximal portion of each of the wearer's legs.

2. The sanitary article according to claim 1 wherein a band-shaped elastic sheet member is attached along the circumference of the opening of each of said side members to form a ring.

3. The sanitary article according to claim 1 wherein each of said side members has a slit extending from the inner edge thereof and closed by a tape at the inner edge to form an opening having a restricted length.

* * * * *